United States Patent [19]

Garden

[11] Patent Number: 4,902,510
[45] Date of Patent: Feb. 20, 1990

[54] ECTOPARASITICIDAL POUR-ON FORMULATION

[75] Inventor: Alan R. Garden, Rochester, England

[73] Assignee: Shell Internationale Research Maatschappij B.V., The Hague, Netherlands

[21] Appl. No.: 251,856

[22] Filed: Oct. 3, 1988

[30] Foreign Application Priority Data

Oct. 5, 1987 [GB] United Kingdom ............... 8723347

[51] Int. Cl.$^4$ ........................................... A01N 25/00
[52] U.S. Cl. ....................................... 424/405; 514/68
[58] Field of Search ............... 424/405; 514/30, 65, 514/68, 70

[56] References Cited

U.S. PATENT DOCUMENTS 2,428,494 10/1947 Jones et al. ..................... 514/68
2,429,818 10/1947 Jones et al. ..................... 514/68
4,199,569  4/1980 Chabala et al. .................. 514/30

FOREIGN PATENT DOCUMENTS 0249409  5/1987 European Pat. Off. ............ 424/405
 249409 12/1987 European Pat. Off. .
2065475  7/1981 United Kingdom .
2110092 11/1982 United Kingdom ............... 424/406
2110091  6/1983 United Kingdom .

Primary Examiner—Ellis P. Robinson
Assistant Examiner—P. Prater

[57] ABSTRACT

The invention provides a pour-on formulation comprising a pyrethroid insecticide at a concentration of 7.5 to 75 kg/m$^3$, a $C_{6-15}$ alkanol diester of adipic or phthalic acid at a concentration of 150 to 800 kg/m$^3$, a spreading agent at a concentration of 25 to 300 kg/m$^3$, other additives at a concentration of 0 to 55 kg/m$^3$, the balance being at least 67.5 kg/m$^3$ of a veterinarily-acceptable mineral or vegetable oil having a kinematic viscosity at 40° C. not greater than $35 \times 10^{-6}$ m$^2$/s (35 cSt); a process for the preparation of the formulation; and its application onto a localized region of the skin or coat of an animal for combating ectoparasites.

12 Claims, No Drawings

ECTOPARASITICIDAL POUR-ON FORMULATION

This invention relates to pour-on formulations, their preparation and their application onto localised regions of the skins or coats of animals for control of ectoparasites thereon.

It is known to administer pyrethroid insecticides by a method known as the "pour-on" method, which consists of applying a liquid formulation of the insecticide to a localised region, preferably the dorsal spine, of the skin or coat of an animal to obtain an ectoparasiticidal effect over the whole body of the animal, e.g. GB-A-2 065 475. However not all proposals make use of vehicles which are physiologically well tolerated by the animal body. Thus the preferred formulation of GB-A-2 065 475 comprises 1R cis S-alpha-cyano-3-phenoxybenzyl 2,2-dimethyl-3-(2,2-dichlorovinyl)cyclopropane carboxylate in a 50:50 v/v mixture of olive oil and N,N-dimethylformamide. N,N-dimethyl-formamide is known to be irritating to skin, eyes and mucous membranes and the vapour is known to be harmful, liver injury having been found to occur on prolonged inhalation of 100 ppm (The Merck Index, 9th Ed., 1976, Merck & Co. Inc. NJ, USA).

There is a continuing need to provide effective pour-on formulations based on readily available components which are non-toxic in use on the animals to which they will be applied.

According to the present invention there is provided a pour-on formulation comprising a pyrethroid insecticide at a concentration of 7.5 to 75 kg/m$^3$, a C$_{6-15}$ alkanol diester of adipic or phthalic acid at a concentration of 150 to 800 kg/m$^3$, a spreading agent at a concentration of 25 to 300 kg/m$^3$, other additives at a concentration of 0 to 55 kg/m$^3$, the balance being at least 67.5 kg/m$^3$ of a veterinarily-acceptable mineral or vegetable oil having a kinematic viscosity at 40° C. not greater than 35×10$^6$ m$^2$/S (35cST).

Preferred pyrethroid insecticides have the formula

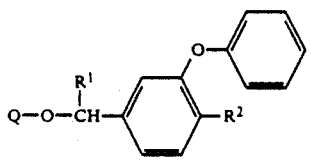

(I)

wherein R$^1$ represents a hydrogen atom or a cyano group, R$^2$ is a hydrogen or fluorine atom and Q is a group of formula

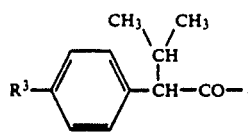

(II)

wherein R$^3$ is a chlorine atom or a difluoromethoxy group, or Q is a group of formula

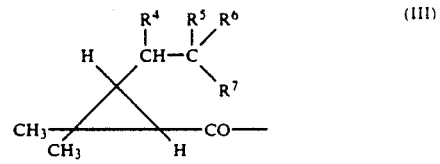

(III)

wherein R$^4$ and R$^5$ together represent a single chemical bond or each represents a bromine atom and R$^6$ and R$^7$ are independently selected from fluorine, chlorine and bromine atoms, and methyl, trifluoromethyl and 4-chlorophenyl groups.

Preferred compounds of formula I include permethrin (R$^1$=R$^2$=H; Q=III; R$^4$ and R$^5$ are a single chemical bond; R$^6$=R$^7$=Cl), cypermethrin (R$^1$=CN; R$^2$=H; Q=III; R$^4$ and R$^5$ are a single chemical bond; R$^6$=R$^7$=Cl), alphacypermethrin ("FASTAC") (Registered Trade Mark) (1R cis S- and 1S cis R-isomers of cypermethrin), cyhalothrin (R$^1$=CN; R$^2$=H; Q=III; R$^4$ and R$^5$ are a single chemical bond; R$^6$=Cl; R$^7$=CF$_3$), cyhalothrin ((S)(Z)-(1R)-cis- and (R)(Z)-(1S)-cis-isomers), deltamethrin (R$^1$=CN; R$^2$=H; Q=III; R$^4$ and R$^5$ are a single chemical bond; R$^6$=R$^7$=Br; 1R cis S-isomer), fenvalerate (R$^1$=CN; R$^2$=H; Q=II; R$^3$=Cl); flucythrinate (R$^1$=CN; R$^2$=H; Q=II; R$^3$=CF$_2$HO—), phenothrin (R$^1$=R$^2$=H; Q=III; R$^4$ and R$^5$ are a single chemical bond; R$^6$=R$^7$=CH$_3$), cyphenothrin (R$^1$=CN; R$^2$=H; Q=III, R$^4$ and R$^5$ are a single chemical bond; R$^6$=R$^7$=CH$_3$), flumethrin (R$^1$=CN, R$^2$=F; Q=III; R$^4$ and R$^5$ are a single chemical bond; R$^6$=Cl; R$^7$=4-chlorophenyl), cyfluthrin (R$^1$=CN; R$^2$=F; Q=III; R$^4$ and R$^5$ are a single chemical bond; R$^6$=R$^7$=Cl), tralomethrin (R$^1$=CN; R$^2$=H; Q=III; R$^4$=R$^5$=R$^6$=R$^7$=Br) and tralocythrin (R$^1$=CN; R$^2$=H; Q=III; R$^4$=R$^5$=Br; R$^6$=R$^7$=Cl).

Most preferred compounds of formula I are those wherein R$^1$ represents a cyano group, R$^2$ represents a hydrogen atom, Q is a group of formula III, R$^4$ and R$^5$ together represents a single chemical bond, and R$^6$ and R$^7$ are both chlorine atoms, ie. cypermethrin and, preferably, alphacypermethrin.

Preferably the pyrethroid insecticide is present at a concentration of 10 to 30 kg/m$^3$, most advantageously 15 kg/m$^3$.

Advantageously the alkanol diester is present at a concentration of 250 to 600 kg/m$^3$. Preferably the weight ratio of pyrethroid insecticide: alkanol diester is in the range 1:15 to 1:30. When the pyrethroid insecticide is present at a concentration of 15 kg/m$^3$, the alkanol diester is preferably present at a concentration in the range 280 to 450 kg/m$^3$, more preferably 280 to 310 kg/m$^3$.

Preferably the alkanol diester is a C$_{7-13}$ alkanol diester of adipic or phthalic acid, e.g. the dialkyl phthalates of blends of C$_{7-9}$, C$_{7-11}$ or C$_{9-11}$ primary alcohols (e.g. "Linevol" DL 79P, DL 711P or DL 911P) ("Linevol" is a registered trade mark), and the dialkyl phthalates and adipates of 2-ethylhexanol, iso-octanol, 3,5,5-trimethylhexanol, isodecanol and tridecanol. Di-isoctyl phthalate and di-2-ethylhexyl adipate have been found to give very good results.

The spreading agent is preferably a polyoxyethylene polyol fatty acid ester or a silicone oil, e.g. a polydimethyl cyclosiloxane, and is preferably present at a concentration of 30 to 250 kg/m³, advantageously 30 to 70 kg/m³, e.g. 30 to 50 kg/m³.

The kinematic viscosity of a mineral oil at 40° C. is preferably not greater than $20 \times 10^{-6}$ m²/s (20 cSt). (Measurement of kinematic viscosity at 40° C. is according to ISO 3104.). Corn oil of the specified viscosity is an example of a suitable vegetable oil.

The other additives may comprise stabilising agents, e.g. antioxidants; co-toxicants, e.g. organophosphorus compounds such as bromophos-ethyl, chlorfenvinphos, phoxim, fenitrothion, fenchlorphos, ethion, coumaphos, chlorpyrifos, crotoxyphos and bromophos methyl; or colouring agents. When included, one or more colouring agents are preferably present in an amount up to 5 kg/m³.

As other additive, it is preferred to include a co-toxicant in the form of ivermectin. Ivermectin is a semi-synthetic derivative of the avermectins, containing at least 80% w of 22,23-dihydroavermectin $B_{1a}$ and less than 20% w of 22,23-dihydroavermectin $B_{1b}$, and is described in The Merck Index, Tenth Edition, Merck & Co., Inc., New Jersey, USA (1983) and U.S. Pat. No. 4,199,569. Ivermectin is preferably present at a concentration of 1 to 10 kg/m³, more preferably 1.5 to 7.5 kg/m³, most preferably 2.5 to 5.0 kg/m³. Conveniently the weight ratio ivermectin:pyrethroid insecticide is in the range 1:8 to 1:4, advantageously about 1:6.

Formulations in accordance with the invention typically have a density of about 900 kg/m³.

The invention also provides a process for the preparation of the pour-on formulation according to the invention defined above which comprises dissolving the pyrethroid insecticide in at least part of the alkanol diester and admixing the resulting solution with the remaining components of the formulation.

The invention further provides a method of combating animal ectoparasites, e.g. ticks, flies, lice and keds, which comprises applying a pour-on formulation according to the invention defined above onto a localised region of the skin or coat of an animal, e.g. selected from cattle, sheep, goats, pigs, dogs, horses, deer and cats.

Application may be by painting, spraying, pouring or by means of a dosing gun or syringe, conveniently to the back of the animal, e.g. in a line along the middle of the back of the animal between the base of the neck and base of the tail.

The invention will be further understood from the following illustrative Examples.

EXAMPLE 1

A pour-on formulation was prepared having the following composition:

|  | g/l (kg/m³) |
|---|---|
| Alphacypermethrin | 15 |
| "Arlatone T" (trade mark) spreading agent | 30 |
| Dioctyl adipate (di-2-ethylhexyl adipate) (DOA) | 290 |
| "Ondina 15" (trade mark) oil | to 1 liter |

"Arlatone T" spreading agent is a polyoxythylene polyol fatty acid ester, being defined as polyoxyethylene 40 septaoleate. "Ondina 15" oil is a refined white mineral oil, kinematic viscosity at 40° C., ISO 3104, $15 \times 10^{-6}$ m²/s (15cSt); density at 15° C., ISO 3675, 0.865 kg/l; flash point, closed, ISO 2719, 157° C.; refractive index, $n_D^{20}$, DIN 51 432-1, 1.467.

The alphacypermethrin was dissolved in the dioctyl adipate, and the "Arlatone T" spreading agent and "Ondina 15" oil were blended into the resulting solution until the formulation was homogeneous. The resulting formulation was stable.

EXAMPLES 2 TO 5

By the process of Example 1 were prepared pour-on formulations having the following compositions:

|  | g/l (kg/m³) | | | |
|---|---|---|---|---|
| Example | 2 | 3 | 4 | 5 |
| Alphacypermethrin | 20 | 15 | 20 | 30 |
| "Arlatone T" spreading agent | 30 | 100 | 100 | 250 |
| DOA | 375 | 290 | 375 | 475 |
| "Ondina 15" oil | to 1 l. | to 1 l. | to 1 l. | to 1 l. |

In each case the resulting formulation was homogenous and stable.

EXAMPLE 6

A pour-on formulation was prepared having the following composition:

|  | g/l (kg/m³) |
|---|---|
| Alphacypermethrin | 15 |
| "Silicone 344" (trade mark) spreading agent | 50 |
| Di-isooctylphthalate | 300 |
| "Ondina 15" oil | to 1 l. |

"Silicone 344" spreading agent is a polydimethylcyclosiloxane.

The alphacypermethrin was dissolved in the di-isooctylphthalate and the "Silicone 344" spreading agent and "Ondina 15" oil were blended into the resulting solution until the formulation was homogeneous. The resulting formulation was stable.

EXAMPLES 7 TO 9

By equivalent procedures to those of Examples 1 to 5 there were prepared the following formulations:

|  | g/l (kg/m³) | | |
|---|---|---|---|
| Example | 7 | 8 | 9 |
| Cypermethrin | 15 | — | — |
| Alphacypermethrin | — | 15 | 10 |
| "Arlatone T" spreading agent | 30 | 30 | 30 |
| DOA | 400 | 450 | 300 |
| "Ondina 15" oil | to 1 l. | — | — |
| Corn oil | — | to 1 l. | to 1 l. |

The corn oil was a refined deodourised maize oil ex Beoco Ltd., Bootle, U.K., specification code 70MZ10 of kinematic viscosity at 40° C., ISO 3104, $33.4 \times 10^{-6}$ m²/S (33.4cSt), free fatty acids (as oleic acid) 0.1 max., colour (Lovibond) 5¼ inch (13.3 cm) cell 2.0 to 5.0 red units, iodine value 118 to 128.

In each case the resulting formulation was homogenous and stable.

EXAMPLES 10 TO 12

By equivalent procedures to those of Examples 1 to 9, the ivermectin being added with the alphacypermethrin, there were prepared the following formulations:

| Example | g/l (kg/m³) | | |
|---|---|---|---|
| | 10 | 11 | 12 |
| Alphacypermethrin | 15 | 30 | 30 |
| Ivermectin | 2.5 | 5 | 5 |
| "Arlatone T" spreading agent | 30 | 30 | 30 |
| DOA | 290 | 580 | 500 |
| "Ondina 15" oil | to 1 l | to 1 l | — |
| Corn oil | — | — | to 1 l |

The corn oil was as in Examples 8 and 9.
In each case the resulting formulation was homogenous and stable.

COMPARATIVE EXAMPLES A AND B

By equivalent procedures to those of Examples 1 to 5 there were prepared the following formulations:

| A | g/l (kg/m³) |
|---|---|
| Alphacypermethrin | 15 |
| "Arlatone T" spreading agent | 30 |
| "Linevol phthalate DL79P" (trade mark) | 400 g |
| "Ondina 68" (trade mark) oil | to 1 l. |

"Linevol phthalate DL 79P" is the dialkyl phthalate of a blend of $C_{7-9}$ primary alcohols, refractive index $n_D^{20}$ 1.4850.

"Ondina 68" oil is a refined white mineral oil, kinematic viscosity at 40° C., ISO 3104, $68 \times 10^{-6}$ m²/s (68 cSt); density at 15° C., ISO 3675, 0.882 kg/l; flash point, closed, ISO 2719, 227° C.; refractive index, $n_D^{20}$, DIN 51 432-1, 1.478.

| B | g/l (kg/m³) |
|---|---|
| Alphacypermethrin | 20 |
| DOA | 375 |
| "Ondina 15" oil | to 1 l. |

EXAMPLE 13

Pour-on formulations were evaluated in stall trials for efficacy against cattle tick, *Boophilus microplus*. The strain of *Boophilus microplus* used was the strain BIARRA, an organophosphate-resistant, DDT-susceptible, strain.

Cattle, calves of mixed Friesian/Hereford stock, weighing 100–150 kg, were artificially infested with *B. microplus* larvae over a three-week period. During the whole period of the tests the cattle were kept in treatment groups, 3 or 4 animals per group, in roofless pens constructed so as to allow collection of dropping fully engorged female ticks.

The pour-on formulations were applied on the basis of volume to animal weight (live weight of the animal), the calculated volume being applied with a dosing gun or syringe in a line along the middle of the back of the animal between the base of the neck and the base of the tail.

Assessment of product efficacy was made over 21 days after application of the pour-on formulation, in comparison with untreated control animals. Two types of measurement were made:

(i) reduction in the number of engorged female ticks ("adult tick control") collected from each treated group of animals on a daily basis compared with the number collected from the group of untreated control animals. (This figure is corrected if necessary by the ratio between the numbers of engorged female ticks from the respective groups of animals over one or two days prior to application of the pour-on formulations).

(ii) reduction in egg weight and viability of eggs from surviving engorged ticks collected from the treated group in comparison with those from the control group.

Overall control of the tick population is assessed by combining the two measurements and calculating the overall reduction in tick survival over the 21 day period after application.

Assessment was made by the above method by application of pour-on formulations at a rate of 20 ml/100 kg animal body weight (equivalent to 0.3 g alphacypermethrin/100 kg) using the formulation of Example 1 and that of Comparative Example A. Results are given in Table I.

TABLE I

| Pour-on formulation | Adult tick control % | Overall control % |
|---|---|---|
| Example 1 | 90.9 | 92.1 |
| Comparative A | 46.1 | 57.3 |

Thus the formulation containing the lower viscosity oil ("Ondina 15") was very much more effective than that containing the higher viscosity oil ("Ondina 68").

EXAMPLE 14

Assessment was made by the test procedure of Example 13 using the pour-on formulation of Example 2 and that of Comparative Example B, but applying the formulations at a rate of 10 ml/100 kg (equivalent to 0.2 g alphacypermethrin/100 kg). Results are given in Table II.

TABLE II

| Pour-on formulation | Adult tick control % | Overall control % |
|---|---|---|
| Example 2 | 82.1 | 85.6 |
| Comparative B | 70.7 | 72.3 |

These results demonstrate the positive effect of the presence of "Arlatone T" spreading agent in the pour-on formulation of Example 2.

EXAMPLE 15

Assessment was made by the test procedure of Example B using the pour-on formulations of Examples 1, 3, 4, 5 and 6, with application at volume rate equivalent to 0.3 g alphacypermethrin/100 kg animal body weight. Results are given in Table III.

TABLE III

| Pour-on formulation | Volume/ 100 kg | Adult tick control % | Overall control % |
|---|---|---|---|
| Example 1 | 20 | 96.6 | 98.4 |
| Example 3 | 20 | 90.5 | 94.5 |
| Example 4 | 15 | 91.0 | 94.5 |
| Example 5 | 10 | 91.5 | 94.5 |

TABLE III-continued

| Pour-on formulation | Volume/ 100 kg | Adult tick control % | Overall control % |
|---|---|---|---|
| Example 6 | 20 | 96.7 | 98.7 |

It will be observed that there are differences in control given in Tables I and III for the pour-on formulation of Example 1. In this connection it should be noted that the test on the formulation of Example 1 in Example 13 was conducted in the autumn, whereas those on the formulations of Examples 1, 3, 4, 5 and 6 in Example 15 were conducted in the spring.

I claim:

1. A pour-on formulation comprising at a concentration of 7.5 to 75 kg/m$^3$, a pyrethroid insecticide, which has the formula

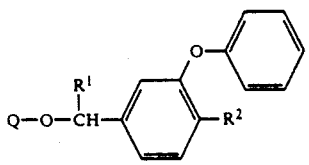

wherein $R^1$ represents a hydrogen atom or a cyano group, $R^2$ is a hydrogen or fluorine atom and Q is a group of formula

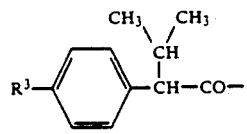

wherein $R^3$ is a chlorine atom or a difluoromethoxy group, or Q is a group of formula

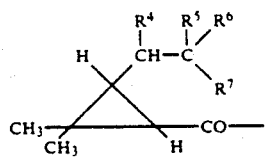

wherein $R^4$ and $R^5$ together represent a single chemical bond or each represents a bromine atom and $R^6$ and $R^7$ are independently selected from fluorine, chlorine and bromine atoms, and methyl, trifluoromethyl and 4-chlorophenyl groups; a $C_{6-15}$ alkanol diester of adipic or phthalic acid at a concentration of 150 to 800 kg/m$^3$; a spreading agent selected from the group consisting of a polyoxyethylene polyol fatty acid ester and a silicone oil at a concentration of 25 to 300 kg/m$^3$; other additives at a concentration of 0 to 55 kg/m$^3$, the balance being at least 67.5 kg/m$^3$ of a verterinarily-acceptable mineral or vegetable oil having a kinematic viscosity at 40° C. not greater than $35 \times 10^{-6}$ m$^2$/s (35 cSt).

2. A pour-on formulation according to claim 1 wherein $R^1$ represents a cyano group, $R^2$ represents a hydrogen atom, Q is a group of formula III, $R^4$ and $R^5$ together represent a single chemical bond, and $R^6$ and $R^7$ are both chlorine atoms.

3. A pour-on formulation according to claim 1 or 2 wherein the pyrethroid insecticide is present at a concentration of 10 to 30 kg/m$^3$.

4. A pour-on formulation according to claim 1 or 2 wherein the alkanol diester is present at a concentration of 250 to 600 kg/m$^3$.

5. A pour-on formulation according to claim 1 or 2 wherein the alkanol diester is a $C_{7-13}$ alkanol diester of adipic or phthalic acid.

6. A pour-on formulation according to claim 1 or 2 wherein the spreading agent is present at a concentration of 30 to 250 kg/m$^3$.

7. A pour-on formulation according to claim 1 or 2 wherein the kinematic viscosity of the mineral oil at 40° C. is not greater than $20 \times 10^{-6}$ m$^2$/s (20 cSt).

8. A pour-on formulation according to claim 1 wherein ivermectin is present, as other additive, at a concentration of 1 to 10 kg/m$^3$.

9. A pour-on formulation according to claim 8 wherein the ivermectin is present at a concentration of 1.5 to 7.5 kg/m$^3$.

10. A pour-on formulation according to claim 9 wherein the ivermectin is present at a concentration of 2.5 to 5.0 kg/m$^3$.

11. A process for the preparation of a pour-on formulation according to claim 1 which comprises dissolving the pyrethroid insecticide in at least part of the alkanol diester and admixing the resulting solution with the remaining components of the formulation.

12. A method of combating animal ectoparasites which comprises applying a pour-on formulation according to claim 1 onto a localised region of the skin or coat of an animal.

* * * * *

UNITED STATES PATENT AND TRADEMARK OFFICE
CERTIFICATE OF CORRECTION

PATENT NO. : 4,902,510

DATED : February 20, 1990

INVENTOR(S) : ALAN R. GARDEN

It is certified that error appears in the above-identified patent and that said Letters Patent is hereby corrected as shown below:

On the cover page, under "Foreign Application Priority Data" add

--Apr. 21, 1988 [GB] United Kingdom..... 8809435--

Signed and Sealed this

Twenty-ninth Day of January, 1991

Attest:

HARRY F. MANBECK, JR.

*Attesting Officer*   *Commissioner of Patents and Trademarks*